United States Patent [19]
Requejo et al.

[11] Patent Number: 6,019,804
[45] Date of Patent: Feb. 1, 2000

[54] COMPRESSION-MOLDED CANDLE PRODUCT

[75] Inventors: Luz P. Requejo, Racine, Wis.; Kathryn H. Ferguson, Chicago, Ill.; Keith G. Patzen, Union Grove, Wis.; Bradley Matyas, Brantford, Canada

[73] Assignee: S. C. Johnson & Son, Inc., Racine, Wis.

[21] Appl. No.: 08/978,220

[22] Filed: Nov. 25, 1997

[51] Int. Cl.[7] .................................. C10L 5/00; F23D 3/16
[52] U.S. Cl. ............................ 44/275; 431/288; 431/289
[58] Field of Search .............................. 44/275; 431/288, 431/289

[56] References Cited

U.S. PATENT DOCUMENTS

| | | | |
|---|---|---|---|
| 2,638,411 | 5/1953 | Thompson | 44/275 |
| 2,807,524 | 9/1957 | Tench | 44/275 |
| 2,825,635 | 3/1958 | Dooley | 44/275 |
| 2,831,330 | 4/1958 | Walker | 44/275 |
| 3,246,963 | 4/1966 | Merz | 44/275 |
| 3,613,658 | 10/1971 | Knowles | 44/275 |
| 4,314,915 | 2/1982 | Wiegers et al. . | |
| 4,411,829 | 10/1983 | Schulte-Elte . | |
| 4,434,306 | 2/1984 | Kobayashi . | |
| 4,614,625 | 9/1986 | Wilson . | |
| 4,696,676 | 9/1987 | Wilson et al. | 44/275 |
| 4,714,496 | 12/1987 | Luken | 44/275 |
| 4,855,098 | 8/1989 | Taylor | 44/275 |

FOREIGN PATENT DOCUMENTS 57-002398  1/1982  Japan .

*Primary Examiner*—D. Gabrielle Brouillette
*Assistant Examiner*—Cephia D. Toomer

[57] ABSTRACT

This invention provides a prilled wax composition that can be compression-molded to a votive type candle product which has a superior combination of density and hardness properties. An invention receptacle-contained votive candle can have a burn rate between about 2 and 5 grams per hour with a standard cotton wick, and maintains a flame height between about 1–3 centimeters during combustion.

13 Claims, No Drawings

6,019,804

COMPRESSION-MOLDED CANDLE PRODUCT

BACKGROUND OF THE INVENTION

This invention generally relates to the dispensing of an air freshener from a candle product. More specifically this invention relates to a process for manufacturing a compression-molded candle product having a high content of air freshener ingredient.

Candles have been known and used since early civilization. A typical candle is formed of a solid or semi-solid body of wax such as paraffin wax or beeswax, and it contains an axially embedded combustible fibrous wick.

When the wick of a candle is lit, the generated heat melts the solid wax, and the resulting liquid flows up the wick by capillary action and is combusted.

More recently candles have been developed that appeal to the olfactory as well as the visual sense. This type of candle usually incorporates a fragrance oil in the wax body. As the wax is melted in a lighted candle, there is a release of the fragrance oil from the liquefied wax pool.

Conventional fragrance candles have drawbacks because of cost and other considerations. The incorporation of fragrance oil in candle wax is difficult to achieve in a quantity which ensures the release of a suitable level of fragrance into the atmosphere during candle burning. Further, the incorporated fragrance tends to migrate and volatilize from the wax body prematurely. The fragrance also softens the wax body, and there is an undesirable loss of rigidity in the candle structure.

Candles typically are prepared by means of melt-processing. For purposes of commercial-scale manufacture, there can be economic advantage in the prospective utilization of wax powder compression technology. However, the production of a superior candle product by wax powder compression is not readily achieved. The compression-molding of a wax powder is affected by formulation variables such as wax melting point, particle size distribution, the number and quantity of additives such as air fresheners and colorants, and the like, and process variables such as compression time and the degree of compression.

There is continuing interest in the development of candle products which can be manufactured by means of improved powder compression technology.

Accordingly, it is an object of this invention to provide a prilled wax composition which is adapted for candle manufacture by compression-molding.

It is another object of this invention to provide a compression-molded candle product which has a high content of air freshener ingredient, and which has a beneficial combination of hardness and superior burning properties.

Other objects and advantages of the present invention shall become apparent from the accompanying description and examples.

DESCRIPTION OF THE INVENTION

One or more objects of the present invention are accomplished by the provision of a prilled wax composition comprising (a) between about 60–92 weight percent of refined paraffin wax having a melting point in the range of about 55°–65° C. and a maximum oil content of about 0.5 percent, (b) between about 2–20 weight percent of microcrystalline wax having a melting point in the range of about 65°–96° C., (c) between about 3–20 weight percent of $C_{14}$–$C_{20}$ fatty acid ingredient, (d) between about 0–10 weight percent of air freshener ingredient, and (e) between about 0–2 weight percent of colorant ingredient; wherein at least about 85 weight percent of the prilled wax particles have a particle size distribution in the range between about 600–1190 microns, and wherein the prilled wax composition has a powder density between about 0.50–0.65 gram per cubic centimeter.

A preferred prilled wax composition has an air freshener content between about 2–20 weight percent.

Prilled wax particles typically are formed by first melting a blend of solid wax ingredients in a vessel, and then spraying the molten wax medium through a nozzle into either a cooling chamber where the finely dispersed medium solidifies into spherical particles as the dispersion descends in the cooling chamber, or into the air where particles solidify and fall onto the surface of a rotating cooling drum. A process for prilling candle wax is described in U.S. Pat. No. 4,614,625, incorporated by reference.

An essential aspect of a present invention prilled wax composition is a prescribed particle size distribution within the range defined hereinabove. The product of a prilled wax process can be subjected to a particle size classification procedure, and the appropriate particle size class can be selected and formulated for the purpose of a present invention prilled wax composition.

One or more of the $C_{14}$–$C_{20}$ fatty acid, air freshener and colorant ingredients can be added prior to the molten wax prilling stage, or the ingredients can be added after the prilling stage as illustrated in U.S. Pat. No. 4,614,625.

The refined paraffin wax and microcrystalline wax ingredients of an invention prilled wax composition are commodity items which are commercially available.

The $C_{14}$–$C_{20}$ fatty acid ingredient also is commercially available, usually as a mixture of fatty acids such as stearic acid, palmitic acid and oleic acid.

The colorant is an optional ingredient, and can comprise one or more pigments and dyes in a quantity between about 0.001–2 weight percent of the prilled wax composition. A pigment constituent preferably is an organic toner in the form of a fine powder suspended in a liquid medium such as a mineral oil. A dye constituent normally is dissolved in an organic solvent such as toluene or xylene. A variety of pigments and dyes suitable for candle making are listed in U.S. Pat. No. 4,614,625.

The air freshener ingredient preferably is a liquid fragrance comprising one or more volatile organic compounds which are available from perfumery suppliers such IFF, Firmenich Inc., Takasago Inc., Belmay, Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract.

Scented oil also can be formulated to provide desirable fruity odors, such as lime, lemon or orange.

Synthetic types of fragrance compositions either alone or in combination with natural oils are described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

The air freshener ingredient also can be a liquid formulation containing an insect repellent such as citronellal, or a therapeutic agent such as eucalyptus or menthol.

In another embodiment this invention provides a process which comprises compression-molding a prilled wax composition to form a candle product which has a density between about 0.8–0.9 grams per cubic centimeter, and an ASTM D-2240 hardness value between about 530–795 gram force at 25° C.; wherein the prilled wax composition is a blend of ingredients comprising (a) between about 60–92 weight percent of refined paraffin wax having a melting point in the range of about 55°–65° C. and a maximum oil content of about 0.5 percent, (b) between about 2–20 weight percent of microcrystalline wax having a melting point in the range of about 65°–96° C., (c) between about 3–20 weight percent of $C_{14}$–$C_{20}$ fatty acid ingredient, (d) between about 0–10 weight percent of air freshener ingredient, and (e) between about 0–2 weight percent of colorant ingredient; wherein at least about 85 weight percent of the prilled wax particles have an average particle size distribution in the range between about 600–1190 microns; and wherein the prilled wax composition has a powder density between about 0.55–0.65 grams per cubic centimeter.

Equipment and procedures for wax powder compression are described in publications such as "Powder Compression Of Candles" by M. Kheidr (International Group Inc., 1990), incorporated by reference. Compression-molding can be conducted under conditions comprising a mold pressure between about 1000–4000 psi, a compression time between about 1–20 seconds, and a prilled wax temperature between about 15°–25° C.

The particle size distribution specification of an invention prilled wax composition is critical for achieving a superior combination of properties in the final candle product.

The specified particle size distribution permits the prilled wax composition to have a powder density between about 0.55–0.65 grams per centimeter, and subsequently allows the compression-molded candle product to have a density between about 0.8–0.9 gram per cubic centimeter.

Additionally, the particle size distribution specification of an invention prilled wax composition contributes other important property improvements to the final candle product. A high degree of particle fusion is effected by the compression-molding procedure, and the final candle product is characterized by desirable hardness and strength properties, and by a high gloss or satin candle surface finish.

The present invention also contemplates the incorporation of between about 0.1–5 weight percent of a wax fusion enhancing type of additive in the prilled wax composition which is being subjected to a compression molding procedure. Suitable wax-fusion enhancer additives include benzyl benzoate, dimethyl phthalate, dimethyl adipate, isobornyl acetate, cellusolve acetate, glucose pentaacetate, pentaerythritol tetraacetate, trimethyl-s-trioxane and N-methyl pyrrolidone.

The prill composition additive also has a beneficial effect on the combustion properties of a candle product which is compression molded in accordance with the present invention.

The beneficial effect appears to derive from an improved wick capillarity, which in turn appears to result from a solubilzation effect by the additive on solid organic residue which deposits within the wick capillaries during the burning stage.

In a further embodiment this invention provides a compression-molded candle product which has an axially disposed wick, and which is a fused blend of ingredients comprising (a) between about 60–92 weight percent of refined paraffin wax having a melting point in the range of about 55°–65° C. and a maximum oil content of about 0.5 percent, (b) between about 2–20 weight percent of microcrystalline wax having a melting point in the range of 65°–96° C., (c) between about 3–20 weight percent of $C_{14}$–$C_{20}$ fatty acid ingredient, (d) between about 0–10 weight percent of air freshener ingredient, and (e) between about 0–2 weight percent of colorant ingredient; wherein the candle product has a density between about 0.8–0.9 gram per cubic centimeter, an ASTM D-2240 hardness value between about 530–795 gram force at 25° C.

A preferred candle product has an air freshener content between 2–20 weight percent.

In a further embodiment of the present invention, the candle product can have an applied coating medium (e.g. an overdip) having a thickness between about 0.2–0.9 millimeters on the candle surface.

Suitable coating compositions can include one or more ingredients selected from the group consisting of microcrystalline wax, paraffin wax, natural wax, fatty acids and amides, polyolefins and celluloses.

A present invention candle product is characterized by a superior combination of density and hardness. With respect to combustion performance, a present invention candle product advantageously can maintain a wick flame height between 1–3 centimeters during the period of wick burn.

As another important attribute, a present invention candle product resists any undesirable tunneling effect during combustion. Under wick burn conditions, a molten wax concavity development in the candle matrix typically has a axial depth which does not exceed about 1.7 centimeters.

A present invention candle product can be in the form of a votive which is contained within a glass or metal receptacle, and typically has a diameter between about 1–3 inches and a height between about 1.5–3.5 inches. A present invention receptacle-supported votive can exhibit a burn rate between about 2–5 grams per hour with a centrally positioned braided cotton wick.

The following examples are further illustration of the present invention. The components and specific ingredients are presented as being typical, and various modifications can be derived in view of the foregoing disclosure within the scope of the invention.

The hardness of an invention candle product is measured in accordance with the procedure of modified ASTM D-2240 to determine a gram force value at 25° C. using Durometer Model 410 Type 0.

EXAMPLE I

This Example illustrates the preparation of a prilled wax composition and compression molded candle in accordance with the present invention.

Microcrystalline wax (Victory Lite Wax MP 80° C.); with maximum oil content of 0.5 weight percent, is mixed with a stearic acid (MP 69° C.), the admixture is blended with colorant (Pyla Wax Yellow Brown C-619) and fragrance (IFF Vanilla 5447-HAY). To the pre-blended concentrate mixture, paraffin wax (Bareco FR-5914 MP 58° C.)is added by using in line blending process. The candle wax composition is agitated and heated to 70° C. until the ingredient mixture is homogeneous. The candle wax composition is then pumped to the wax reservoir of a Kurschner wax spray drum, and the composition is held at a temperature of 68°–70° C. The spray drum is set to a speed of 42 meters/min. The spray room temperature is held at no greater than 15° C. and relative humidity of approximately 50%. The candle wax composition is pumped through the spray manifold system from the spray drum reservoir and sprayed at one foot height above the drum so that the wax semi-solidifies before contacting the drum surface. The wax is collected on the spray drum, and then scraped from the drum and transferred into a vibrating conveyor that leads inside the drum for further cooling. The prilled wax is collected at the end of the drum and vacuum fed into the press hopper which of a Kurschner Model 2300 28 station rotary press. For consistent pocket filling and proper compression, the beads are maintained at temperature between about 16–22° C. The targeted weight for candle of 1⅕ by 2 inches dimension is 42–44 grams. This weight is strictly controlled to minimize candle density variability. Candles produced below this target weight do not meet the desired hardness and do not provide the desirable burn characteristics.

The prilled candle wax composition consists of paraffin wax 87 weight percent (Bareco FR-5914 MP 58° C.), microcrystalline wax 3 weight percent (Victory Lite Wax MP 80° C.), stearic acid 7.5 weight percent, 3 weight percent fragrance oil (IFF Vanilla 5447-HAY), and 0.001 weight percent dye colorant (Pyla Wax Yellow Brown C-6190).

The prilled candle wax composition is collected from the spray drum for particle size analysis. In accordance with ASTM method D 1921-89 for particle size analysis, a set of Wire-Cloth sieve screens ranging from screen size 16 to screen size 35 including the pan are assembled, and 100 gram samples of prilled candle wax composition are sieved and calculated for particle distribution. The screen sizes correspond to particle size in microns: 16=1190 microns, 18=1000 microns, 20=840 microns, 25=710 microns, 30=500 microns, and the residual particles in the pan are less than 500 microns in size. Example of desired particle size distribution are the following;

| Sieve Size (Micron) | Percent Table A | Table B |
| --- | --- | --- |
| 16(1190) | 8.8 | 11.7 |
| 18(1000) | 8.7 | 12.9 |
| 20(840) | 10.8 | 12.7 |
| 25(710) | 31.8 | 33.4 |
| 30(600) | 35.7 | 26.7 |
| 35(560) | 1.6 | 1.0 |
| Pan(<500) | 26 | 1.6 |

For purposes of present invention candle product fabrication, a prilled candle wax composition is selected which has at least about 85 weight percent of the prilled wax particles with a particle size distribution in the range between about 600–1190 microns, and which has a powder density of about 0.60 gram per cubic centimeter.

EXAMPLE II

This Example illustrates the preparation of a compression-molded candle product in accordance with the present invention.

The prilled candle wax of Example I is transferred from the spray drum to the fill hopper of a Kurschner Model 2300 28 station rotary press. The press cavities, which pass below the hopper, are filled with prilled wax composition (20° C.) to a depth of 1.42 times the finished height of the candle. The cavities filled with the prilled wax continue the rotary sequence to the compression stage, where the prilled candle wax is subjected to partial to full compression from top and bottom for approximately 2 seconds. The cavities continue the rotary sequence to the extraction stage, where the compressed molded candle is extracted by pushing it up and out of the cavity. The compressed molded candle is then transferred to a Kurschner wicking machine where the wick is inserted into the compressed molded candle. The wick consists of cotton yarn braided with paper wire (Stabilo 4 wick, Technical Braiding GMB, Germany). Stabilo wicks are manufactured in different sizes, which are identified as Stabilo 3, Stabilo 4, Stabilo 5, Stabilo 6, Stabilo 7 Stabilo 8 and Stabilo 10.

The compressed molded candle with the inserted wick is then transferred to a Kurschner over dipping machine. The compressed molded candle is dipped for 1–2 seconds into a first overdip tank, which contains a refined paraffin wax (Bareco FR 5914 MP 70° C.)heated to 92° C. The compressed molded candle is then dipped for 1–2 seconds into a second tank, which contains a fragranced wax blend (Bareco FR-5914 MP 70° C. and IFF 5447-HAY) and uninhibitor.

Compressed molded is to read-compressed molded candle is dipped into water (20° C.) for 1–2 seconds. The bottom of the compressed molded candle is then leveled by contact with a textured heating plate at 100° C.

The compressed candle product is tested for hardness in accordance with ASTM method D-2240. Samples are tested for the amount of gram force required to A) break the surface of the compressed candle, and B) to penetrate through the surface of candle and into the compressed body of the candle. Samples are collected before and after the overdipping process for correlation of in-line process conditions with the finished candle properties. The candles are tested for overall hardness at the top, middle and bottom of the compressed candle. Samples represent an average of 30 candles per set.

Hardness Test: ASTM D-2240 hardness measurement for rubber industry is modified to determine the candle hardness. Durometer Model 410 Type 0 is used to measure the compressed candle hardness. Measurements are taken from ⅛ inch from top and bottom and the exact bottom of the candle. Two readings are recorded during the test. The first reading is the amount of gram force needed to break the candle surface, and the second reading is the gram force needed to penetrate through the candle.

TABLE

Average Hardness
(Main spring 817 grams force)

| Sample | Bottom: Penetrate | Break | Middle: Penetrate | Break | Top: Penetrate | Break |
| --- | --- | --- | --- | --- | --- | --- |
| A (undipped) | 614.9 | 687.5 | 618.6 | 687.9 | 677.2 | 730.5 |
| B (undipped) | 665.8 | 750.4 | 683.9 | 766.8 | 716.7 | 753.7 |
| C (dipped) | 720.8 | 755.9 | 715.4 | 763.8 | 726.6 | 746.1 |
| D (dipped) | 729.0 | 765.2 | 730.7 | 776.7 | 729.0 | 765.2 |

What is claimed is:

1. A compression-molded candle product which has an axially disposed wick, and which is a fused blend of ingredients comprising (a) between about 60–92 weight percent of refined paraffin wax having a melting point in the range of about 55°–65° C. and a maximum oil content of about 0.5 percent, (b) between about 2–20 weight percent of microcrystalline wax having a melting point in the range of 65°–96° C., (c) between about 3–20 weight percent of $C_{14}$–$C_{20}$ fatty acid ingredient, (d) between about 0–20 weight percent of air freshener ingredient, and (e) between about 0–2 weight percent of colorant ingredient; wherein the candle product has a density between about 0.80–0.90 gram per cubic centimeter, and an ASTM D-2240 hardness value between about 530–795 gram force at 25° C.

2. A candle product in accordance with claim 1 which has a content between about 2–20 weight percent of air freshener ingredient.

3. A candle product in accordance with claim 1 wherein the fatty acid ingredient comprises stearic acid.

4. A candle product in accordance with claim 1 wherein the air freshener ingredient comprises a fragrance composition.

5. A candle product in accordance with claim 1 wherein the air freshener ingredient comprises an insect repellent composition.

6. A candle product in accordance with claim 1 wherein the air freshener ingredient comprises a therapeutic composition.

7. A candle product in accordance with claim 1 which additionally has an applied coating medium having a thickness between about 0.2–0.9 millimeters on the candle surface.

8. A candle product in accordance with claim 1 which under wick burn conditions develops a molten wax concavity having an axial depth which does not exceed about 1.7 centimeters.

9. A candle product in accordance with claim 1 which under wick burn conditions maintains a flame height between about 1–3 centimeters during combustion.

10. A compression molded candle product which has an axially disposed wick, and which is a fused blend of ingredients comprising (a) between 60–92 weight percent of refined paraffin wax having a melt point in the range of about 55°–65° C. and a maximum oil content of about 0.5 percent, (b) between about 2–20 weight percent of microcrystalline wax having a melting point in the range of 65°–96° C., (c) between about 3–20 weight percent of $C_{14}$–$C_{20}$ fatty acid ingredient, (d) between about 0–20 weight percent of air freshener ingredient, and (e) between about 0–2 weight percent of colorant ingredient; wherein the candle product has a density between 0.8–0.9 grams per cubic centimeter, and as ASTM D-2240 hardness value between about 530–795 gram force at 25° C.; and wherein under wick burn conditions the candle product develops a molten concavity having an axial depth which does not exceed about 1.7 centimeters, and maintains a flame height between about 1–3 centimeters during combustion.

11. A candle product in accordance with claim 10 wherein the candle is a votive which is contained within a glass or metal receptacle.

12. A candle product in accordance with claim 10 wherein the candle is in the form of a receptacle-supported votive having a diameter between about 1–3 inches and a height between 1.5–3.5 inches.

13. A candle product in accordance with claim 10 wherein the candle is a receptacle-supported votive which exhibits a burn rate between about 2 to 5 grams per hour with a braided cotton wick.

\* \* \* \* \*